United States Patent
Booth et al.

(10) Patent No.: US 6,495,529 B1
(45) Date of Patent: Dec. 17, 2002

(54) (−)-PSEUDOEPHEDRINE AS A SYMPATHOMIMETIC DRUG

(75) Inventors: Anthony Booth, Chester, NJ (US); William T. Sherman, Hendersonville, NC (US); Peter Raven, Forth Worth, TX (US); James L. Caffrey, Burelson, TX (US); Thomas Yorio, Burelson, TX (US); Michael Forster, Fort Worth, TX (US); Patricia Gwirtz, Forth Worth, TX (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/743,052

(22) PCT Filed: Jun. 8, 1999

(86) PCT No.: PCT/US99/12692
§ 371 (c)(1),
(2), (4) Date: Jul. 1, 1998

(87) PCT Pub. No.: WO00/01379
PCT Pub. Date: Jan. 13, 2000

Related U.S. Application Data

(60) Provisional application No. 60/091,451, filed on Jul. 1, 1998.

(51) Int. Cl.⁷ ............................................. A61K 31/135
(52) U.S. Cl. ....................... 514/55; 514/648; 514/649; 514/912
(58) Field of Search ................................ 514/648, 649, 514/653, 912

(56) References Cited

U.S. PATENT DOCUMENTS 4,801,461 A * 1/1989 Hamel et al. ................ 424/467
5,354,693 A * 10/1994 Brynes et al. ............... 436/537

FOREIGN PATENT DOCUMENTS

WO 9217171 10/1992

OTHER PUBLICATIONS

Kier; "The Preferred Conformations of Ephedrine Isomers and the Nature of the Alpha Adrenergic Receptor"; J. Pharmacol. Exp. Ther.; vol. 164; No. 1; 164: 75–81; 1968.

Fauley et al.; "The Stereoselective Inhibition of Lipolysis by Nonphenolic Phenethylamines"; Eur. J. Pharmacol. vol. 27; No. 1, 136–140; 1974.

Patil et al.; "Steric Aspects of Adrenergic Drugs. I. Comparative Efects of DL Isomers and Desoxy Derivatives"; J. Pharmacol. Exp. Ther. vol. 155; No. 1; 1–12; 1967.

Lapdius et al.; Steric Aspects of Adrenergic Drugs VII Certain Pharmacological Actions of D(−)–Pseudoephedrine; J. Pharm. Sci., vol. 56, No. 9; 1125–1130; 1967.

Bukowiecki et al.; ephedrine, a potential slimming drug, directly stimulates thermogenesis in brown adipocyctes via β–andrenoreceptors; Int J. Obes; vol. 6, No. 4; 343–350; 1982.

\* cited by examiner

*Primary Examiner*—Zohreh Fay
(74) *Attorney, Agent, or Firm*—Barry H. Jacobsen; Evan J. Federman

(57) ABSTRACT

The present invention provides pharmaceutical compositions which include (−)-pseudoephedrine and a pharmaceutically acceptable carrier, wherein the (−)-pseudoephedrine is substantially-free of (+)-pseudoephedrine. In another embodiment, the present invention provides methods of relieving nasal and bronchial congestion and of inducing pupil dilation which include administering a pharmaceutically effective amount of (−)-pseudoephedrine to a mammal. The (−)-pseudoephedrine used in the present methods is substantially free of (+)-pseudoephedrine and also substantially free of side effects caused by administration of (+)-pseudoephedrine.

10 Claims, 6 Drawing Sheets

Figure 1:
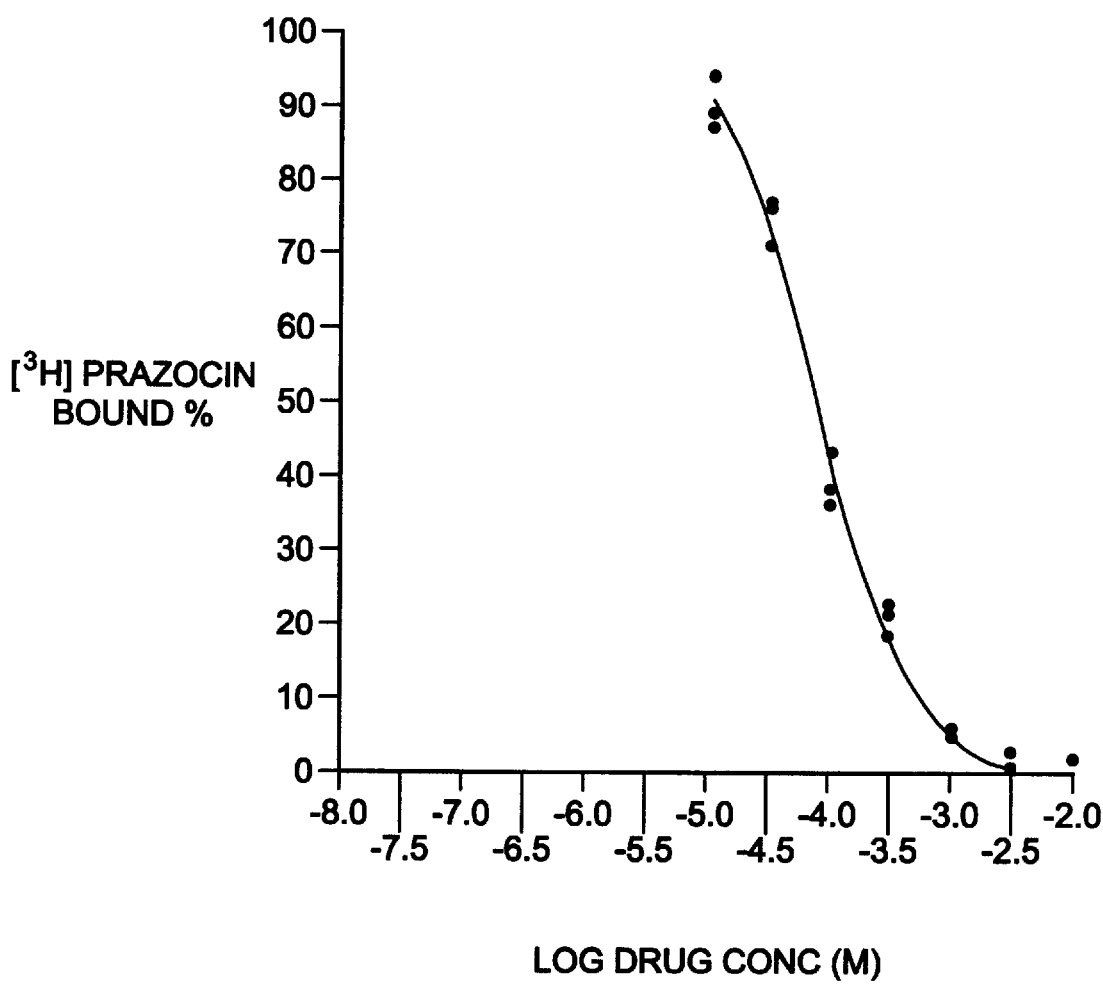

(-) Ψ EPHEDRINE PROJECT COMPOUND # 2
$\alpha_1$-RECEPTOR (canine lung membranes)
(example 03-03-96)

$K_i$ = 33 uM
$IC_{50}$ = 73 uM

FIG-2  (+) Ψ EPHEDRINE PROJECT COMPOUND # 1
$\alpha_1$-RECEPTOR (canine lung membranes)
(example 01-15-96)
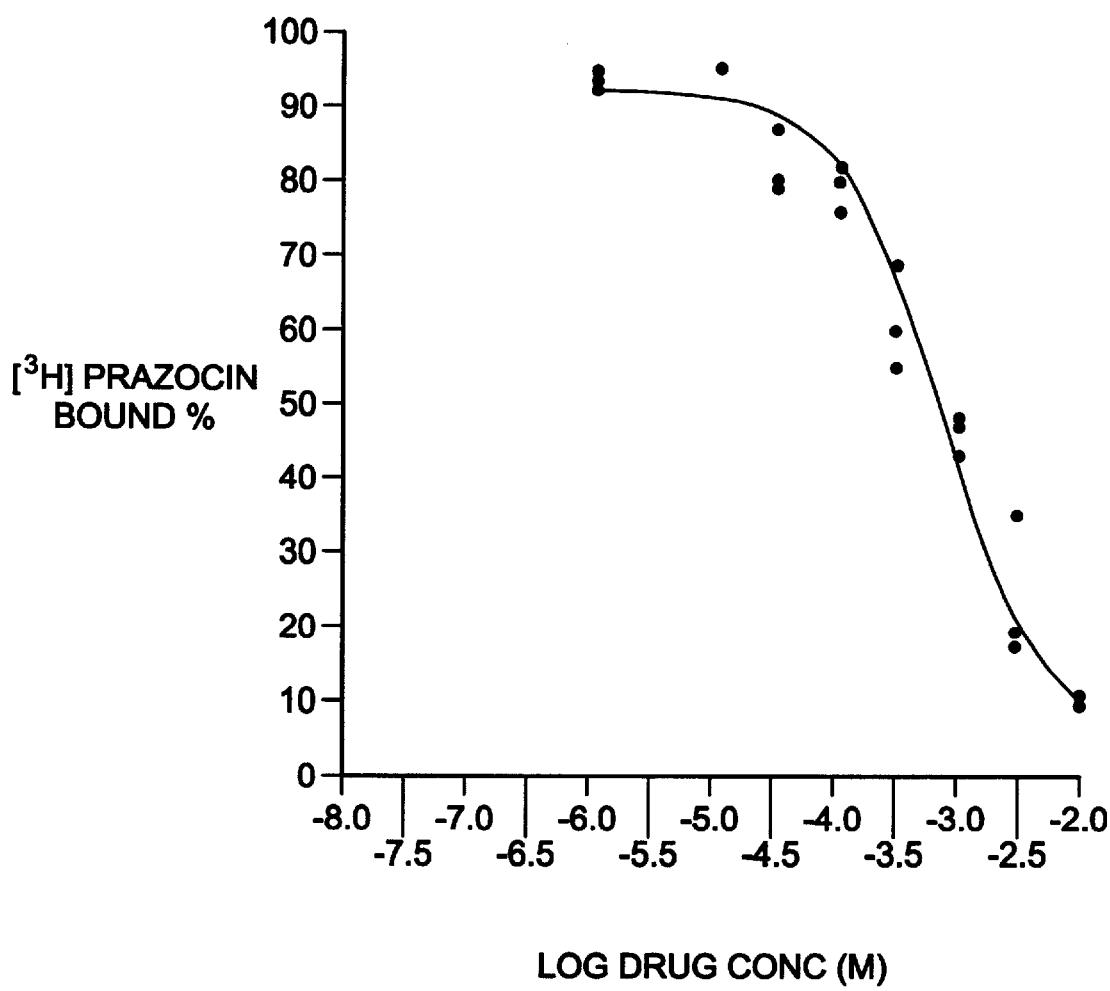
Ki = 349 uM
IC$_{50}$ = 756 uM

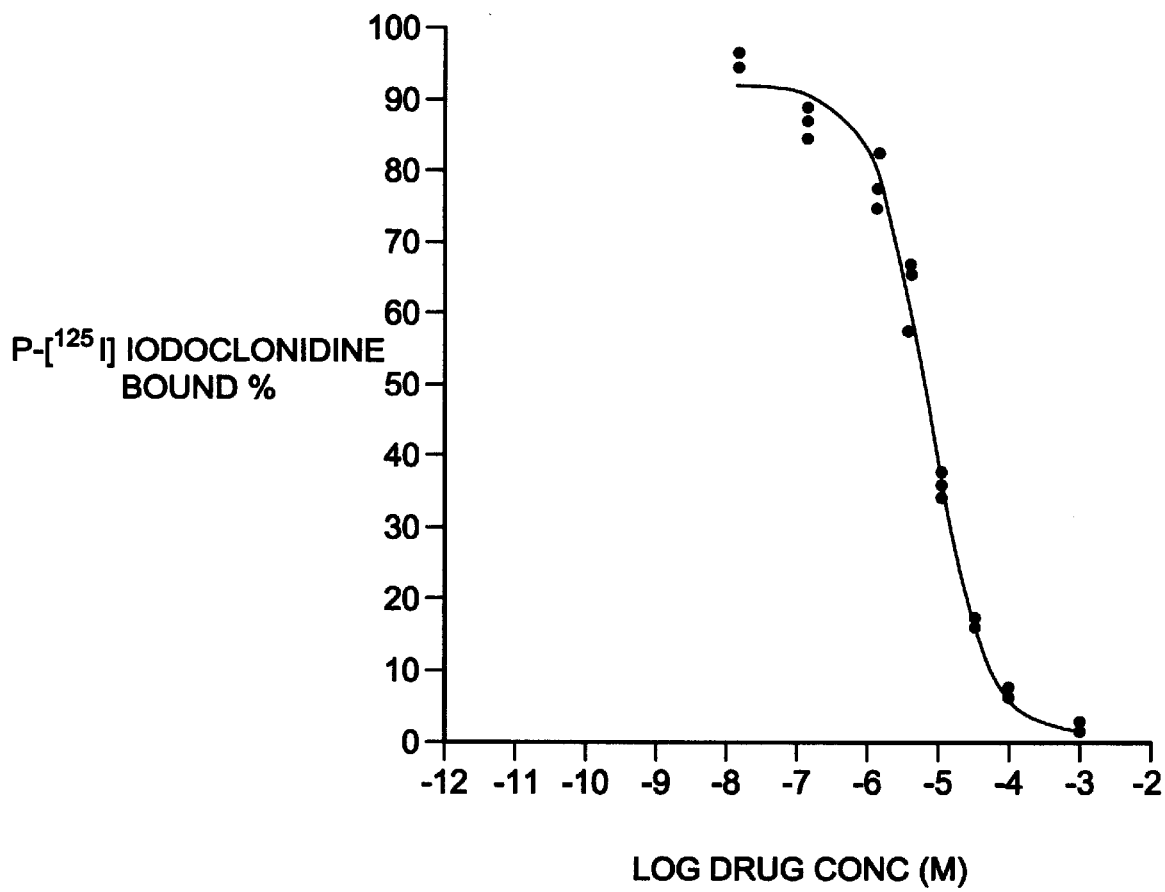

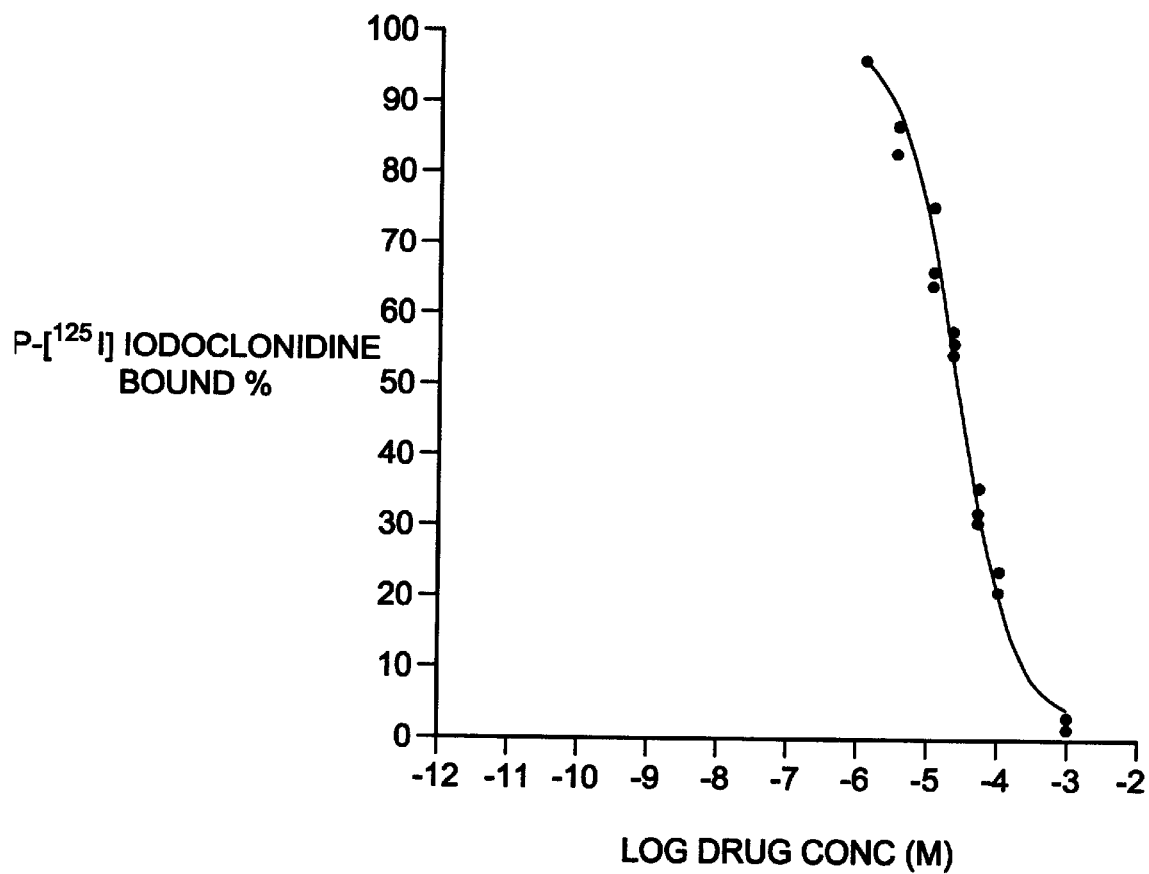
FIG-4 (+) Ψ EPHEDRINE PROJECT COMPOUND # 1
$\alpha_2$-RECEPTOR (canine brain membranes)
(example 05-14-96)
$K_i$ = 17 uM
$IC_{50}$ = 23 uM

FIG-5  (-) Ψ EPHEDRINE PROJECT COMPOUND # 2
$\beta_2$-RECEPTOR (canine lung membranes)
(example 03-19-96)
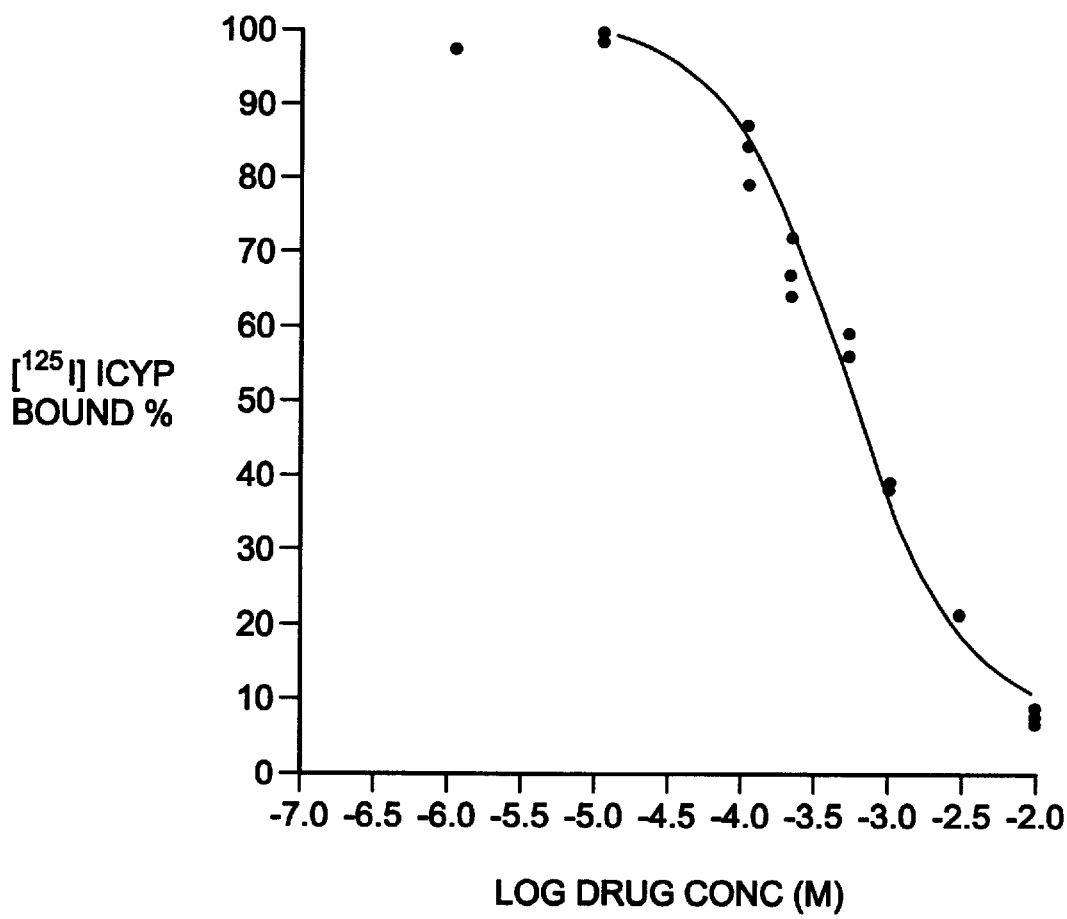
Ki = 213 uM
IC$_{50}$ = 489 uM

FIG-6 (+) Ψ EPHEDRINE PROJECT COMPOUND # 1
$\beta_2$-RECEPTOR (canine lung membranes)
(example 03-19-96)
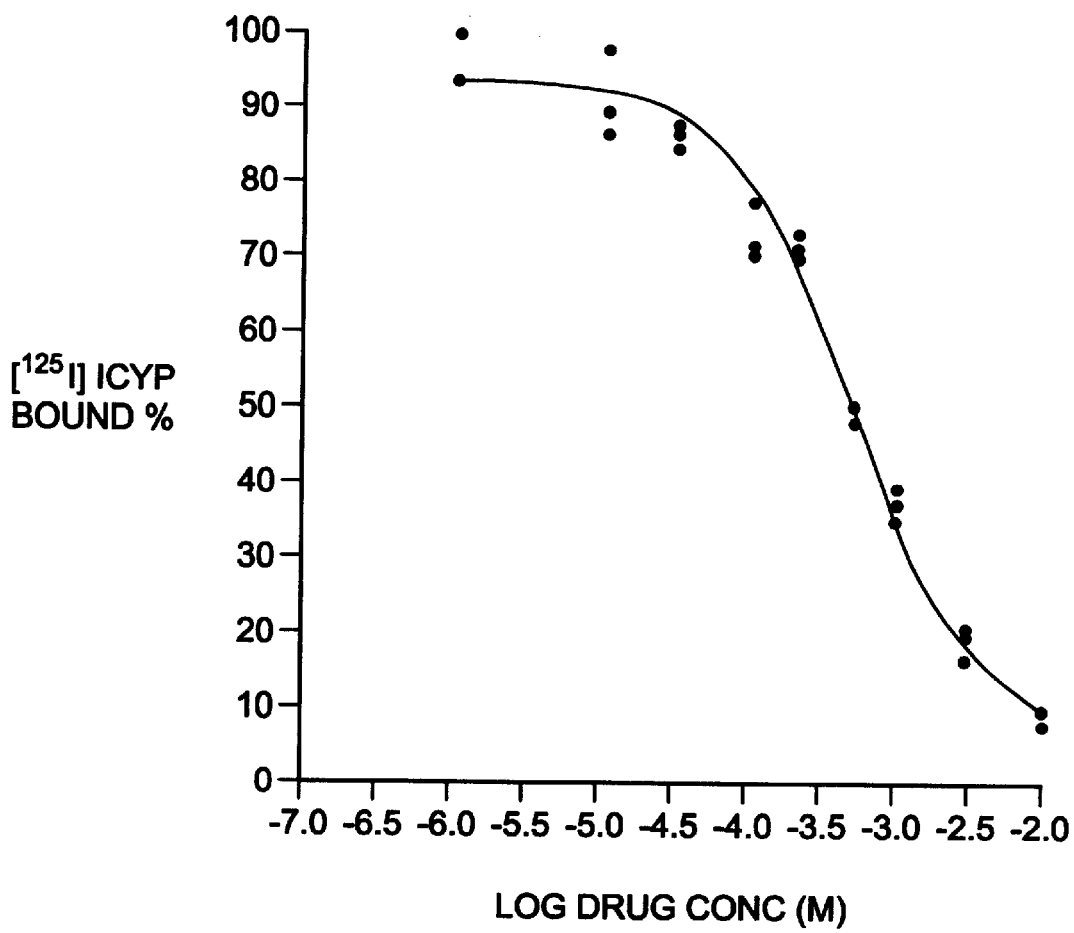
Ki = 223 uM
$IC_{50}$ = 511 uM

(−)-PSEUDOEPHEDRINE AS A SYMPATHOMIMETIC DRUG

This application claims the benefit of provisional application No. 60/091,451, filed Jul. 1, 1998.

FIELD OF THE INVENTION

The present application provides pharmaceutical compositions and methods of using the sympathomimetic composition of (−)-pseudoephedrine as a decongestant, bronchodilator, and the like. The present compositions of (−)-pseudoephedrine are substantially-free of (+)-pseudoephedrine. According to the present invention, at similar doses, (−)-pseudoephedrine binds $\alpha_1$- and $\alpha_2$ adrenergic receptors better than (+)-pseudoephedrine and yet has less adverse effects upon blood pressure and fewer drug interactions.

BACKGROUND OF THE INVENTION

Sympathomimetic drugs are structurally and pharmacologically related to amphetamine. They generally act by binding to or activating $\alpha$- and $\beta$-adrenergic receptors, resulting in vascular constriction, reduced blood flow and/or reduced secretion of fluids into the surrounding tissues. Such receptor binding generally decreases swelling of nasal membranes and the amount of mucous secreted into nasal passages. Sympathomimetic drugs are therefore used to treat nasal congestion, allergies and colds. In addition, they are used as appetite suppressants and mydriatic agents.

At the present time, some drugs are sold as racemic mixtures. Alternatively, the most easily isolated stereoisomer is sold, even though another stereoisomer may have greater activity or fewer side effects because that stereoisomer interacts more selectively with the receptors involved in sympathomimetic action. Isolation and use of the more selective stereoisomer may therefore reduce not only the required dosage, but many unwanted side effects.

Many organic compounds exist in optically active forms. This means that they have the ability to rotate the plane of plane-polarized light. An optically active compound is often described as a chiral compound. Such a chiral compound has at least one asymmetric carbon which can exist in two different, mirror image configurations. Compounds which have the same composition but are mirror images of each other are called enantiomer. The prefixes d and l, or (+) and (−), identify the direction in which an enantiomer rotates light. The d or (+) steroisomer, or enantiomer, is dextrorotatory. In contrast, the l or (−) enantiomer is levorotatory. A mixture of (+) and (−) enantiomers is called a racemic mixture.

An alternative classification system for stereoisomers exists where prefixes (S) and (R) are used. This classification system is based on the structure of the compound.

(+)-Pseudoephedrine is known to be sympathomimetic amine which binds to $\alpha$-adrenergic receptors. It is sold under the tradename SUDAFED®. However, (+)-pseudoephedrine has undesirable side effects, including central nervous system stimulation, lightheadedness, nervousness, anxiety, paranoia, heart arrhythmia, atrial fibrillations and premature ventricular contractions. 95 American Hospital Formulatory Service 847–48. Moreover, (+)-pseudoephedrine can easily be converted into the controlled drug, (S)-methamphetamine, by simply converting the hydroxyl in (+)-pseudoephedrine to a hydrogen.

Hence, a need exsists for a compsition having the beneficial decongestant activities of (+)-pseudoephedrine, without its adverse side effects, and without its (S)-methamphetamine-conversion problem.

SUMMARY OF THE INVENTION

The present invention is directed to a pharmaceutical composition containing (−)-pseudoephedrine and a pharmaceutically acceptable carrier, wherein the pharmaceutical composition is substantially-free of (+)-pseudoephedrine. Suprisingly, the present (−)-pseudoephedrine compositions bind to $\alpha$-adrenergic receptors with greater affinity than do (+)-pseudoephedrine compositions while causing less adverse effects on blood pressure. Moreover, (−)-pseudoephedrine has decongestant activity which is similar to several known decongestants. The pharmaceutical composition has (−)-pseudoephedrine in a therapeutic dosage suitable for treating nasal or broncial congestion, counteracting the physiological effects of histamine, dilating the pupil, suppressing the appetite, treating attention deficit hyperactivity disorder and treating other conditions typically treated with sympathomimetic drugs. Upon administration to a mammal in a therapeutically effect amount, the present compositions may have reduced side effects relative to administration of (+)-pseudoephedrine, for example, interactions with drugs such as antihistamines. Moreover, (−)-pseudoephedrine reduces the (S)-methamphetamine conversion problem of (+)-pseudoephedrine, because reduction of the hydroxyl in (−)-pseudoephedrine results in (R)-methamphetamine with substantially less psychoactivity than (S)-methamphetamine.

The present invention is also directed to a method of relieving nasal and bronchial congestion which includes administering a therapeutically effective amount of (−)-pseudoephedrine to a mammal, wherein such (−)-pseudoephedrine is substantially-free of (+)-pseudoephedrine. This method has less side effects than a method which includes administration of a racemic pseudoephedrine mixture or a composition of (+)-pseudoephedrine. In this embodiment, a therapeutically effective amount of (−)-pseudoephedrine is a dosage suitable for treating nasal and/or bronchial congestion.

The present invention is also directed to a method of antagonizing the physiological effects of histamine which includes administering a therapeutically effective amount of (−)-pseudoephedrine to a mammal, wherein such (−)-pseudoephedrine is substantially-free of (+)-pseudoephedrine. According to the present invention, (−)-pseudoephedrine surprisingly is a physiological antagonist of histamine. This method has fewer side effects than a method which includes administration of a composition including (+)-pseudoephedrine. It is also believed that this method has less side effects than administration of a racemic mixture of (+)- and (−)-pseudoephedrine. In this embodiment, a therapeutically effective amount of (−)-pseudoephedrine is a dosage suitable for relieving the physiological effects of histamine, for example, nasal congestion, inflammation, and other allergic responses.

The present invention is also directed to a method of treating conditions typically treated with sympathomimetic drugs, which includes administering a therapeutically effective amount of (−)-pseudoephedrine to a mammal, wherein such (−)-pseudoephedrine is substantially-free of (+)-pseudoephedrine. This method may have fewer side effects than a method which includes administration of a composition of (+)-pseudoephedrine alone. It is also believed to have fewer side effects than administration of a racemic mixture of (+)- and (−)-pseudoephedrine. In this embodiment, a therapeutically effective amount of (+)-phenylephrine is a dosage suitable for treating the condition typically treated with a sympathomimetic drug.

BRIEF DESCRIPTIONS OF THE DRAWINGS

FIG. 1 provides a graph of the percent prazocin which remains bound to $\alpha_1$-receptors as increasing amounts of (−)-pseudoephedrine (●) is added. Prazocin displacement indicates that a compound binds to $\alpha_1$-receptors. The $IC_{50}$ provides a measure of the amount of drug required for 50% displacement of prazocin. In this example, the $IC_{50}$ for (−)-pseudoephedrine is 33 µM.

FIG. 2 provides a graph of the percent prazocin which remains bound to $\alpha_1$-receptors as increasing amounts of (+)-pseudoephedrine (●) is added. In this example, the $IC_{50}$ for (+)-pseudoephedrine is 349 µM. These results combined with those in FIG. 1, show that the (−)-pseudoephedrine binds to $\alpha_1$-receptors with a greater affinity than (+)-pseudoephedrine.

FIG. 3 provides a graph of the percent iodoclonidine which remains bound to $\alpha_2$-receptors as increasing amounts of (−)-pseudoephedrine (●) is added. Iodoclonidine displacement indicates that a compound binds to $\alpha_2$-receptors. The $IC_{50}$ provides a measure of the amount of drug required for 50% displacement of iodoclonidine. In this example, the $IC_{50}$ for (−)-pseudoephrine is 6.4 µM.

FIG. 4 provides a graph of the percent iodoclonidine which remains bound to $\alpha_2$-receptors as increasing amounts of (+)-pseudoephedrine (●) are added. Iodoclonidine displacement indicates that a compound binds to $\alpha_2$-receptors. In this example, the $IC_{50}$ for (+)-pseudoephedrine is 17 µM. These results combined with those in FIG. 3, show that (−)-pseudoephedrine binds to $\alpha_2$-receptors with a greater affinity than (+)-pseudoephedrine.

FIG. 5 provides a graph of the percent iodocyanopindolol (ICYP) which remains bound to $\beta_2$-receptors as increasing amounts of (−)-pseudoephedrine (●) is added. ICYP displacement indicates that a compound binds $\beta_2$-receptors. The $IC_{50}$ provides a measure of the binding activity of $\beta_2$-receptors for the drug. In this example, the $IC_{50}$ for (−)-pseduoephrine is 213 µM.

FIG. 6 provides a graph of the percent iodocyanopindolol (ICYP) which remains bound to $\beta_2$-receptors as increasing amounts of (+)-pseudoephedrine (●) are added. ICYP displacement indicates that a compound binds $\beta_2$-receptors. In this example, the $IC_{50}$ for (+)-pseudoephedrine is 511 µM. These results, in combination with those in FIG. 5, show that the (−)-pseudoephedrine binds $\beta_2$-receptors with slightly greater affinity than does (+)-pseudoephedrine.

DETAILED DESCRIPTION OF THE INVENTION

The present invention provides pharmaceutical compositions of (−)-pseudoephedrine that are substantially free of (+)-pseudoephedrine. The present invention also provides methods of using such (−)-pseudoephedrine compositions for treating colds, treating nasal congestion, treating allergies, treating histamine-related inflammations, treating obesity, dilating the pupil, and treating other conditions typically treated with sympathomimetic drugs. According to the present invention, the structures of (+)-pseudoephedrine and (−)-pseudoephedrine are:

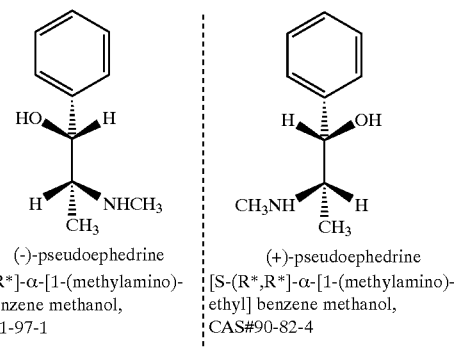

(−)-pseudoephedrine
[R-(R*,R*)]-α-[1-(methylamino)-ethyl] benzene methanol,
CAS#321-97-1

(+)-pseudoephedrine
[S-(R*,R*)]-α-[1-(methylamino)-ethyl] benzene methanol,
CAS#90-82-4

(+)-Pseudoephedrine is known as a decongestant, but it can readily be converted into the psychoactive drug, (S)-methamphetamine, by reduction of the hydroxyl group to hydrogen. Reduction of the hydroxyl in (−)-pseudoephedrine yields a compound with only one-tenth the psychoactivity of (S)-methamphetamine. Hence, the present compositions and methods avoid this problem.

The term "substantially free of (+)-pseudoephedrine" means that the composition contains at least 90% (−)-pseudoephedrine and 10% or less (+)-pseudoephedrine. In a more preferred embodiment, "substantially free of (+)-pseudoephedrine" means that the composition contains at least 95% (−)-pseudoephedrine and 5% or less (+)-pseudoephedrine. Still more preferred is an embodiment wherein the pharmaceutical composition contains 99% or more (−)-pseudoephedrine and 1% or less (+)-pseudoephedrine.

According to the present invention, compositions of (−)-pseudoephedrine which are substantially free of (+)-pseudoephedrine are also substantially free of the adverse side effects related to administration of (+)-pseudoephedrine. Such adverse side effects include but are not limited to interactions with other drugs such as antihistamines. Moreover, when similar amounts of (+)- and (−)-pseudoephedrine are administered, (−)-pseudoephedrine causes fewer cardiovascular side effects. In particular, (−)-pseudoephedrine does not adversely effect blood pressure at the doses of (+)-pseudoephedrine which are normally administered, whereas (+)-pseudoephedrine can adversely increase blood pressure. As a result, administration of the present compositions of (−)-pseudoephedrine produce reduced side effects relative to the administration of the (+)-stereoisomer of pseudoephedrine. It is also believed that administration of the present (−)-pseudoephedrine compositions has fewer side effects relative to the administration of a racemic mixture of (+)- and (−)-pseudoephedrine.

The (−)-pseudoephedrine of this invention may be prepared by known procedures. Methods for separating the stereoisomers in a racemic mixture are well-known to the skilled artisan.

The present invention also provides pharmaceutically acceptable salts of (−)-pseudoephedrine. For example, (−)-pseudoephedrine can be provided as a hydrochloride, bitartrate, tannate, sulfate, stearate, citrate or other pharmaceutically acceptable salt. Methods of making such pharmaceutical salts of (−)-pseudoephedrine are readily available to one of ordinary skill in the art.

The pharmaceutical compositions of the present invention contain (−)-pseudoephedrine with a pharmaceutically acceptable carrier. As used herein, "pharmaceutically acceptable carrier" includes any and all solvents, dispersion media, coatings, isotonic and absorption delaying agents, sweeteners and the like. The pharmaceutically acceptable carriers may be prepared from a wide range of materials including, but not limited to, diluents, binders and adhesives, lubricants, disintegrants, coloring agents, bulking agents, flavoring agents, sweetening agents and miscellaneous materials such as buffers and adsorbents that may be needed in order to prepare a particular therapeutic composition. The use of such media and agents for pharmaceutically active substances is well known in the art. Except insofar as any conventional media or agent is incompatible with the active ingredient, its use in the therapeutic compositions is contemplated.

According to the present invention, (−)-pseudoephedrine does not interact with other drugs, for example, with antihistamines. This is one advantage that the present compositions and methods of using (−)-pseudoephedrine have over compositions and methods of using (+)-pseudoephedrine: (−)-pseudoephedrine does interact with HI antihistamines such as triprolidine, whereas (+)-pseudoephedrine does interact with $H_1$ antihistamines. Due to the lack of such drug interaction, supplementary active ingredients, such as additional antihistamines and decongestants, can be incorporated into the present (−)-pseudoephedrine compositions. The amount of the added antihistamine or decongestant present in the pharmaceutical composition will depend upon the particular drug used. Typical antihistamines include: diphenhydramine; chlorpheniramine; astemizole; terfenadine; terfenadine carboxylate; brompheniramine; triprolidine; acrivastine; and loratadine.

The present invention further contemplates a method of relieving nasal and/or bronchial congestion which comprises administering a therapeutically effective amount of (−)-pseudoephedrine which is substantially free of (+)-pseudoephedrine. Administration of (−)-pseudoephedrine avoids many of the side effects related to administering (+)-pseudoephedrine including drug interactions.

According to the present invention, (−)-pseudoephedrine is surprisingly effective as a physiological antagonist of histamine. This means (−)-pseudoephedrine counteracts the physiological effects of histamine. Histamine can cause nasal congestion, bronchial congestion, inflammation and the like. This present invention contemplates (−)-pseudoephedrine to counteract all of these histamine-related physiological responses. Moreover, according to the present invention (−)-pseudoephedrine can be combined with antihistamines, for example, antihistamines that bind to $H_1$ antihistamine receptors.

The present invention also contemplates a method of treating inflammation and/or sinus congestion which comprises administering a therapeutically effective amount of (−)-pseudoephedrine. The pharmaceutical compositions of (−)-pseudoephedrine used for this method are substantially-free of (+)-pseudoephedrine and induce less side effects than does administration of a composition containing (+)-pseudoephedrine.

According to the present invention, a therapeutically effective amount of (−)-pseudoephedrine is an amount sufficient to relieve the symptoms of a condition which can be treated by a sympathomimetic drug. In one embodiment, an amount sufficient to reduce the symptoms of a condition which can be treated by a sympathomimetic drug is an amount of (−)-pseudoephedrine sufficient to bind or activate an adrenergic receptor, for example, and α- or a β-adrenergic receptor. When the condition is nasal congestion the therapeutically effective amount is the amount needed to reduce nasal congestion. When bronchial congestion is the condition, the therapeutically effective amount is the amount needed to reduce bronchial congestion or provide bronchodilation. When inflammation and/or allergic reaction is the condition, the therapeutically effective amount is the amount needed to counteract the physiological effects of histamine. When eye pupil dilation is the desired, such as therapeutically effective amount of (−)-pseudoephedrine is an amount of (−)-pseudoephedrine sufficient to dilate the pupil. Preferably, such a pharmaceutically effective amount also produces less side effects than are observed upon administration of (+)-pseudoephedrine, or a racemic mixture of (+)- and (−)-pseudoephedrine. The skilled artisan can readily determine the necessary therapeutically effective amounts for treating these conditions, particularly in light of the teachings provided herein.

The pharmaceutical compositions of the present invention contain (−)-pseudoephedrine in a therapeutically effective amount that is sufficient to provide decongestion, bronchodilation, treat inflammation, produce a mydriatic response or provide appetite suppression while having less side effects than would similar doses of (+)-pseudoephedrine or the racemic mixture of (+)- and (−)-pseudoephedrine. Such a therapeutically effective amount would be about 0.1 micrograms (μg) to about 50 milligrams (mg) per kg of body weight per day and preferably of about 1.0 μg to about 10 mg per kg of body weight per day. More preferably the dosage can range from about 10 μg to about 5 mg per kg of body weight per day. Dosages can be readily determined by one of ordinary skill in the art and can be readily formulated into the subject pharmaceutical compositions.

The subject (−)-pseudoephedrine may be administered by any convenient route. For example, (−)-pseudoephedrine may be inhaled, ingested, topically applied or parenterally injected. The subject (−)-pseudoephedrine may be incorporated into a cream, solution or suspension for topical administration. (−)-Pseudoephedrine is preferably inhaled or administered orally or topically. The skilled artisan can readily determine the route for a specific use.

The following examples further illustrate the invention.

EXAMPLE 1

α-Adrenergic and α-Adrenergic Receptor Binding Studies

Many physiological processes are mediated by the binding of chemical compounds $\alpha_1$ $\alpha_2$ and $\beta_2$ receptors. For example, many compounds which reduce nasal congestion bind to $\alpha_1$ and $\alpha_2$ receptors and some reduce bronchial congestion by binding to $\beta_2$ receptors. Accordingly, a compound that binds to $\alpha_1$ or $\alpha_2$ and/or P2 receptors may be an effective nasal or bronchial decongestant.

More specifically, $\alpha_2$ adrenergic receptors, concentrated on precapillary arterioles in the nasal mucosa, induce arteriolar vasoconstriction when activated by a sympathomimetic compound. Such vasoconstriction decreases blood flow through those vessels and reduces excess extracellular fluid associated with nasal congestion and a runny nose. On the other hand, $\alpha_1$ adrenergic receptors are concentrated on postcapillary venules in the nasal mucosa. Binding to a, receptors induces venoconstriction, which also reduces nasal congestion.

Compounds that bind to $\beta_2$ receptors may also help relieve the symptoms of bronchial congestion because $\beta_2$ receptor binding is related to increased bronchodilation and reduced airway resistance.

The binding of (−)-pseudoephedrine to various $\alpha_1$ $\alpha_2$ and $\beta_2$ receptors was compared to the receptor binding of (+)-pseudoephedrine, (−)-phenylephrine and (−)-ephedrine. The (+) isomer of pseudoephedrine is a known decongestant, sold under the trade name SUDAFED®. (−)-Phenylephrine (Neo-Synephrine®) and (−)-ephedrine are also known to be effective decongestants.

Methods

Membrane Preparations

Pulmonary ALPHA-1 and BETA-2 Receptors.

The lungs of mongrel dogs were separated from cartilaginous airways and major blood vessels, weighted, chopped and placed into 10 volumes of ice-cold buffered sucrose (50 mM Tris-HCl pH 7.4, 1 mM EGTA, 0.32 M Sucrose). The tissue was then homogenized in a Polytron tissue homogenizer. The homogenate was filtered through two layers of cheesecloth, and the filtrate was dounced three times using a Con-Turque Potter homogenizer. The dounced filtrate was centrifuged at 1000×g for 15 min at 4° C. The supernatant was recentrifuged at 30,000×g for 30 min at 4° C. and the resulting pellet was washed and resuspended in 10 volumes of Tris buffer (50 mM Tris HCL, pH 7.4, 1 mM EGTA) and incubated at 37° C. for 30 min in a shaking water bath. The suspension was centrifuged at 4° C., at 30,000×g for 30 min and the resulting pellet washed in 10 volumes of Tris buffer. The final pellet was resuspended in 0.5 volume of 50 mM Tris HCL, pH 7.4, 1 mM EGTA, 25 mM $MgCl_2$. Protein concentration was then determined by the Lowry method and the final suspension was adjusted to 10 mg of protein/ml, aliquoted and stored at −90° C.

Particulated were also prepared for $\beta_2$ receptors using the identical procedure except the final protein concentration was adjusted to 0.1 mg/ml.

Brain ALPHA-2 Receptors

Membranes of mongrel dogs were harvested from the canine frontal cortex and prepared as described for lung except that the final membrane protein concentration was adjusted to 0.5 mg/ml.

Binding Assays

ALPHA-1 Binding, $^3$H-Prazocin

Canine lung membranes (500 μg protein/100 μl) were incubated with $^3$H-Prazocin (77.9 Ci/mmol) for 60 min at 25° C., in a final volume of 0.25 ml of buffer (50 mM Tris-HCl/1 mM EGTA, pH 7.4). Nonspecific binding was determined for each concentration point in separate incubations, with 10 μM phentolamine. Each experimental point was determined in triplicate. The final concentration of $^3$H-Prazocin was 0.7–1.1 nM in competition studies and between 0.1 and 10 nM in saturation experiments. All binding assay incubations were terminated by rapid dilution with 2 ml of ice-cold wash buffer (50 mM Tris-HCl, pH 7.4) and filtration through Whatman GF/B filters using Brandel receptor-binding harvester. The filters were washed twice more with 4 ml of wash buffer and then added to 6 ml Cytoscint (ICN, Costa Mesa Calif.) for liquid scintillation counting (Barnes et al., 1983). In all experiments less than 17% of the added radio ligand was bound, and specific binding was about 65–70% of total binding.

ALPHA-2 Binding P-$^{125}$ Iodoclonidine ($^{125}$ICYP) Canine brain membranes (50 μg protein/100 μl) were incubated with p-iodoclonidine (2200 Ci/mmol) for 120 min at 25° C. in a final volume of 0.25 ml. Nonspecific binding was determined in separate incubations in the presence of 10 μM phentolamine. The final concentration of p-iodoclonidine was 44–45 pM in competition studies and between 50 pM and 10 nM in saturation experiments. Bound and free $^{125}$ICYP were separated and the bound quantitated as described above for the ICYP assays. An average of 6% of radioligand was bound, and specific binding was about 91% of total binding.

BETA-2 Binding, $^{125}$Iodocyanopindolol ($^{125}$ICYP)

Canine lung membranes (10 μg protein/100 μl) were incubated with $^{125}$ICYP (2200 Ci/mmol) for 110 min at 30° C. in a final volume of 0.25 ml. Nonspecific binding was determined in separate incubations in the presence of 2 μM dipropranolol. Each experimental point was determined in triplicate. The final concentration of $^{125}$ICYP was 8–12 pM in competition studies and between 2 and 200 pM in saturation experiments. Incubations were terminated as described above for the $\alpha_1$ assays. Filters were placed into polyethylene tubes and the bound ligand was determined by gamma spectrometry (Sano et al., 1993). An average of 27% of radioligand was bound, and specific binding was about 90% of total binding.

All data were analyzed with the aid of microcomputer nonlinear curve fitting programs (PRISM 2.0, Graphpad Software, San Diego Calif.).

Results

The receptors resident in each of the three membrane preparations were evaluated by standard saturation analysis following the addition of increasing concentrations of the appropriate radioligand. In the case of the $\alpha_1$- and $\beta_2$-assays the mathematical analysis was consistent with a one site fit. The $\alpha_2$-receptor analysis was best fit as two sites, one high and one low affinity.

The radio ligand added for subsequent $\alpha_2$-displacement assays was adjusted to evaluate only the high affinity receptor. Contributions from p-iodoclonidine binding to imidazoline receptors in the $\alpha_2$-displacement assay were evaluated with epinephrine. Epinephrine easily displaced all bound p-iodoclonidine which indicates that at the concentrations employed, p-iodoclonidine labeled few if any imidazoline receptors. Similarly, with the $\beta_2$-assay, contributions from the binding of ICYP to $\beta_1$ sites was evaluated with the $\beta_1$-selective antagonist, atenolol. Atenolol was largely ineffective in displacing ICYP from pulmonary membranes indicating little if any $\beta_1$ binding within the assay. All subsequent analyses with displacement by individual test compounds used the $K_d$ determined from the saturation analysis since it is generally considered a more reliable estimate of the true equilibrium dissociation constant.

Table 1 provides the binding characteristics of the $\alpha_1$-receptors in the membrane preparation for prazocin. The $K_d$ is the apparent equilibrium dissociation constant for prazocin. The $B_{max}$ is the number of $\alpha_1$-receptor binding sites for prazocin in this membrane preparation expressed as femtomoles per mg protein.

TABLE 1

$\alpha_1$-Receptor Binding Characteristics
(canine lung membranes)

| Measure | Summary |
|---|---|
| Scatchard Analysis | |
| $K_d$ | 0.84 nM |
| $B_{max}$ | 55 |
| Saturation Analysis | |
| $K_d$ | 0.73 nM |
| $B_{max}$ | 53 |

Table 2 provides the binding characteristics of the $\alpha_2$-receptors in the membrane preparation for p-iodoclonidine. The $K_d$ is the apparent equilibrium dissociation constant for p-iodoclonidine. The $B_{max}$ is the number of $\alpha_2$-receptor binding sites for p-iodoclonidine in this membrane preparation to expressed as femtomoles per mg protein. Note that the two site data from the Saturation Analysis is more reliable than the Scatchard Analysis because the Scatchard Analysis assumes only one site. In order to obtain both values from the Scatchard plots, the points in the transition zone were arbitrarily divided and assigned to high and low affinity plots.

TABLE 2

$\alpha_2$-Receptor Binding Characteristics
(canine cerebral cortex membranes)

| Measure | Summary |
|---|---|
| Scatchard Analysis | |
| $K_{d1}$ (high affinity) | 0.15 nM |
| $K_{d2}$ (low affinity) | 0.87 nM |
| $B_{max1}$ (high affinity) | 67 |
| $B_{max2}$ (low affinity) | 120 |
| Saturation Analysis | |
| $K_{d1}$ (high affinity) | 0.15 nM |
| $K_{d2}$ (low affinity) | 3.01 nM |
| $B_{max1}$ (high affinity) | 57 |
| $B_{max2}$ (low affinity) | 73 |

Table 3 provides the binding characteristics of the $\beta_2$-receptors in the membrane preparation for $^{125}$iodocyanopindolol (ICYP). The $K_d$ is the apparent equilibrium dissociation constant for ICYP. The $B_{max}$ is the number of $\beta_2$-receptor binding sites for ICYP in this membrane preparation expressed as femtomoles per mg protein.5

TABLE 3

$\beta_2$-Receptor Binding characteristics (canine lung membranes)

| Measure | Run 1 | Run 2 | Summary |
|---|---|---|---|
| Scatchard Analysis | | | |
| $K_d$ | 9.9 pM | 7.8 pM | 8.9 pM |
| $B_{max}$ | 150 | 139 | 145 |

TABLE 3-continued $\beta_2$-Receptor Binding characteristics (canine lung membranes)

| Measure | Run 1 | Run 2 | Summary |
|---|---|---|---|
| Saturation Analysis | | | |
| $K_d$ | 9.6 pM | 9.3 pM | 9.5 pM |
| $B_{max}$ | 149 | 142 | 146 |

FIGS. 1 and 2 provides graphs of the percent prazocin which remains bound to $\beta_2$-receptors as the amounts of (+)-pseudoephedrine and (−)-pseudoephedrine, respectively, increase. Prazocin is commonly known to effectively bind $\alpha_1$-receptors. Competitive displacement of prazocin from $\alpha_1$-receptors is used to assess the strength and effectiveness of $\alpha_1$-receptor binding. The $IC_{50}$ provides a measure of the binding activity of $\alpha_1$ receptors for a drug; it is defined as the amount of the drug in micromoles ($\mu$M) required to inhibit 50% of prazocin binding. In general, the lower the $IC_{50}$, the better the receptor binds the drug.

Here, the $IC_{50}$ for (−)-pseudoephedrine is 33 $\mu$M while that for (+)-pseudoephedrine is 349 $\mu$M, indicating that $\alpha_1$ receptors may have a much greater binding affinity for (−)-pseudoephedrine than for (+)-pseudoephedrine.

FIGS. 3 and 4 provide a graph of the percent iodoclonidine which remains bound to $\alpha_2$-receptors as the amounts of (+)-pseudoephedrine and (−)-pseudoephedrine, respectively, increase. Iodoclonidine is commonly known to effectively bind $\alpha_2$-receptors. Competitive displacement of iodoclonidine from $\alpha_2$-receptors is used to assess the strength and effectiveness of $\alpha_2$-receptor binding. The $IC_{50}$ provides a measure of the binding activity of $\alpha_2$-receptors for a drug; it is defined as the amount of the drug in micromoles ($\mu$M) required to inhibit 50% of iodoclonidine binding. In general, the lower the $IC_{50}$, the better the receptor binds the drug.

Here, the $IC_{50}$ for (−)-pseudoephrine is 0.008 $\mu$M while that for (+)-pseudoephrine is 17 $\mu$M, indicating that $\alpha_2$-receptors may have a much greater binding affinity for (−)-pseudoephedrine than for (+)-pseudoephedrine.

FIGS. 5 and 6 provide graphs of the percent iodocyanopindolol (ICYP) which remains bound to $\beta_2$-receptors as the amounts of (+)-pseudoephedrine and (−)-pseudoephedrine, respectively, increase. ICYP is commonly known to effectively bind $\beta_2$-receptors. Competitive displacement of ICYP from $\beta_2$-receptors is used to assess the strength and effectiveness of $\beta_2$-receptor binding for a drug. The $IC_{50}$ provides a measure of the binding activity of $\beta_2$-receptors for the drug; it is defined as the amount of the drug in micromoles ($\mu$M) required to inhibit 50% of ICYP binding. In general, the lower $IC_{50}$, the better the receptor binds the drug.

Here, the $IC_{50}$, for (−)-pseudoephrine is 489 $\mu$M while that for (+)-pseudoephedrine is 511 $\mu$M.

The $IC_{50}$ and $K_i$ values $\alpha_1$ $\alpha_2$ and $\beta_2$-receptors (−)-pseudoephedrine are compared to (−)-ephedrine, (−)-phenylephrine and (+)-pseudoephedrine in Table 4. The $K_i$ for each compound is based on the relationship $K_i = IC_{50} \div (1 + I/K_d)$, where I is the concentration of tracer added and the $K_d$ is the equilibrium dissociation constant empirically determined for this receptor population.

TABLE 4

| Drugs | Alpha-1 | | Alpha-2 | | Beta-2 | | Ki-Ratio | | |
|---|---|---|---|---|---|---|---|---|---|
| | $IC_{50}$ | $K_i$ | $IC_{50}$ | $K_i$ | $IC_{50}$ | $K_i$ | $\alpha1/\alpha2$ | $\alpha1/\beta2$ | $\beta2/\alpha2$ |
| (−)-Pseudoephedrine | 98 | 48 | 6.0 | 4.6 | 542 | 237 | 10.43 | 0.20 | 51.52 |
| (+)-Pseudoephedrine | 691 | 299 | 28 | 21 | 502 | 220 | 14.23 | 1.35 | 10.48 |
| (−)-Phenylephrine | 7 | 3 | 0.02 | 0.015 | 10 | 5 | 200.0 | 0.60 | 333.3 |
| (−)-Ephedrine | 109 | 47 | 0.77 | 0.59 | 12 | 5 | 79.67 | 9.40 | 8.47 |

These data indicate that (−)-psuedoephedrine binds to $\alpha_1$ and $\alpha_2$ receptors with greater affinity than does (+)-pseudoephedrine.

EXAMPLE 2

(−)-Pseudoephedrine Induces Pupil Dilation without Increasing Intraocular Pressure The induction of pupil dilation or mydriasis by (−)-pseudoephedrine was compared to that caused by (+)-pseudoephedrine, (−)-phenylephrine and (−)-ephedrine. The (+)enantiomer of psuedephedrine is known to be a mydriatic agent which may, unfortunately, cause side effects like an increase in intraocular pressure (IOP). According to the present invention, (−)-pseudoephedrine causes mild pupil dilation without causing the increased IOP associated with (+)-pseudoephedrine administration.

Methods

Enantiomers (−)-pseudoephedrine, (+)-pseudoephedrine, (−)-phenylephrine and (−)-ephedrine were evaluated for their efficacy in producing mydriasis and for their effects on IOP. These agents were administered topically as either 1 and 2% solutions in buffered saline. Pupillary diameter and IOP were measured in all animals over a six hour time period during the day to minimize diurnal variations in IOP and pupil diameter.

The experiments were performed on adult male New Zealand white rabbits, weighing 3.0–6.0 kg. All rabbits were caged individually and maintained on a 12 hr/12 hr light/dark schedule with free access to food and water. All animal procedures were in conformity with the ARVO Resolution on the Use and Care of Animals in Research. All treated rabbits had served as controls by having received a saline treatment on a different day.

Drug or saline-control solutions were applied to the superior aspect of the globe in a volume of 25 µl and allowed to spread over the cornea and sclera, while a conjunctival trough was formed by retracting the lower eyelid for approximately 30 seconds. Only one eye received drug treatment. The contralateral eye served as a control. Saline (or phosphate buffered saline) and drug treated rabbits were treated, and observed simultaneously. A single dose was given at 0 time and IOP and pupil diameter measured at −1.0, −0.5, 0.5, 1, 3 and 5 hrs post-treatment.

IOP measurements were recorded with an Alcon Applanation Pneumotonograph (Surgical Products Division, Alcon Laboratories, Inc., Ft. Worth, Tex.) in rabbits placed in Lucite restraining cages. Initial topical application of a two drop 0.5% proparacaine HCl (OPHTHETIC®, Allergan Pharmaceuticals, Inc.) was performed on each rabbit.

Pupil diameter was measured visually at the point of the greatest horizontal diameter with a transparent millimeter ruler. All measurements were made under the identical ambient lighting conditions.

Mean and Standard Error values were used to construct time-response and dose-response curves for the treated and contralateral eye of research rabbits. The data were analyzed statistically by an analysis of variance and a Bonferoni's test for significance. $P<0.05$ was the accepted level of significance.

Results

Although some variation in baseline IOP was noted among the rabbits tested, there were no significant changes in IOP or pupil diameter (PD) in the saline control groups (Tables 5–7) during the six hour time period selected for drug testing.

The adrenergic agonist (+)-pseudoephedrine is known to be an active sympathomimetic amine which has both α- and β-agonist activity. In this study, (+)-pseudoephedrine produced mydriasis in the treated eye. A slight acute elevation in IOP in the treated eye was observed following 1% and 2% topical application of (+)-pseudoephedrine. A delayed elevation in IOP was also observed in the contralateral eye.

(−)-Pseudoephedrine also produced mydriasis in the treated eye only. Little or no increase in intraocular pressure was observed when administering (−)-pseudoephedrine.

(−)-Ephedrine increased IOP but had no effect on pupil diameter.

TABLE 5

| | | IOP in mmHg | | | | | |
|---|---|---|---|---|---|---|---|
| Time in Hr. | | −1 | −0.5 | 0.5 | 1 | 3 | 5 |
| SALINE (15) | U | 27 ± 0.9 | 25 ± 0.4 | 26 ± 1.5 | 25 ± 1.4 | 27 ± 0.9 | 26 ± 1.2 |
| | T | 26 ± 0.9 | 25 ± 1.1 | 26 ± 1.1 | 25 ± 1.3 | 27 ± 0.8 | 26 ± 0.8 |
| SALINE (15) | U | 20 ± 0.7 | 19 ± 0.9 | 20 ± 1.0 | 19 ± 1.0 | 20 ± 1.0 | 19 ± 1.1 |
| | T | 19 ± 0.8 | 18 ± 0.9 | 18 ± 0.8 | 17 ± 0.7 | 19 ± 0.9 | 18 ± 1.1 |

TABLE 5-continued

IOP in mmHg

| Time in Hr. | | −1 | −0.5 | 0.5 | 1 | 3 | 5 |
|---|---|---|---|---|---|---|---|
| DRUG (1%) | | | | | | | |
| (−)-Pseudoephedrine | U | 21 ± 1.6 | 20 ± 1.4 | 21 ± 1.4 | 19 ± 1.3 | 19 ± 1.0 | 18 ± 1.1 |
| | T | 23 ± 1.8 | 24 = 1.7 | 25 ± 0.5 | 24 ± 1.0 | 22 ± 0.6 | 21 ± 0.7 |
| (+)-Pseudoephedrine | U | 19 ± 1.0 | 18 ± 1.6 | 18 ± 2.0 | 19 ± 1.2 | 20 ± 2.0 | 21 ± 0.9 |
| | T | 20 ± 0.2 | 20 ± 1.7 | 19 ± 2.3 | 22 ± 1.4 | 21 ± 2.0 | 23 ± 2.3 |
| (−)-Phenylephrine | U | 16 ± 1.0 | 15 ± 2.1 | 18 ± 1.6 | 19 ± 1.3 | 20 ± 1.9 | 19 ± 1.7 |
| | T | 20 ± 1.6 | 16 ± 1.5 | 24 ± 0.6 | 24 ± 1.0 | 23 ± 1.5 | 21 ± 1.9 |
| (−)-Ephedrine HCL | U | 19 ± 1.7 | 17 ± 1.0 | 20 ± 1.9 | 19 ± 1.2 | 16 ± 0.9 | 15 ± 1.0 |
| | T | 22 ± 2.0 | 23 ± 0.9 | 23 ± 2.5 | 26 ± 1.0 | 24 ± 0.6 | 23 ± 0.9 |
| DRUG (2%) | | | | | | | |
| (+)-Pseudoephedrine | U | 18 ± 1.0 | 15 ± 1.0 | 18 ± 2.0 | 16 ± 1.2 | 17 ± 1.1 | 16 ± 0.6 |
| | T | 22 ± 1.1 | 18 ± 1.2 | 17 ± 1.2 | 19 ± 1.8 | 17 ± 1.2 | 18 ± 1.7 |
| (+)-Pseudoephedrine | U | 20 ± 1.0 | 16 ± 10 | 18 ± 2.3 | 17 ± 2.1 | 18 ± 1.2 | 22 ± 1.4 |
| | T | 24 ± 1.1 | 18 ± 1.4 | 26 ± 0.8 | 23 ± 1.3 | 22 ± 2.1 | 23 ± 2.4 |
| (−)-Phenylephrine | U | 17 ± 1.9 | 17 ± 1.9 | 20 ± 2.0 | 20 ± 2.4 | 14 ± 1.7 | 14 ± 2.0 |
| | T | 18 ± 1.6 | 15 ± 1.5 | 12 ± 0.8 | 14 ± 2.0 | 16 ± 0.8 | 14 ± 1.3 |
| (−)-Ephedrine HCL | U | 17 ± 1.2 | 19 ± 0.9 | 19 ± 1.4 | 19 ± 1.9 | 18 ± 0.7 | 19 ± 1.5 |
| | T | 16 ± 2.0 | 16 ± 0.7 | 16 ± 1.0 | 15 ± 0.4 | 17 ± 0.7 | 19 ± 0.8 |

Results are as mean ± S.E. of five-six rabbits per drug.
U = Untreated contralateral eye
T = Drug treated eye

TABLE 6

Pupil Diameter in mm

| Time in Hr. | | −1 | −0.5 | 0.5 | 1 | 3 | 5 |
|---|---|---|---|---|---|---|---|
| SALINE | U | 5 ± 0.2 | 5 ± 0.2 | 5 ± 0.2 | 5 ± 0.2 | 5 ± 0.2 | 5 ± 0.2 |
| (15) | T | 5 ± 0.2 | 5 ± 0.2 | 5 ± 0.2 | 5 ± 0.2 | S ± 0.2 | 5 ± 0.2 |
| SALINE | U | 5 ± 0.2 | 5 ± 0.2 | 5 ± 0.2 | 5 ± 0.2 | 5 ± 0.2 | 5 ± 0.2 |
| (15) | T | 5 ± 0.2 | 5 ± O.2 | 5 ± 0.2 | 5 ± 0.2 | 5 ± 0.2 | 5 ± 0.2 |
| DRUG (1%) | | | | | | | |
| (−)-Pseudoephedrine | U | 7 ± 0.2 | 7 ± 0.2 | 7 ± 0.2 | 7 ± 0.2 | 7 ± 0.2 | 7 ± 0.2 |
| | T | 7 ± 0.2 | 7 ± 0.2 | 8 ± 0.2 | 8 ± 0.2 | 8 ± 0.2 | 8 ± 0.2 |
| (+)-Pseudoephedrine | U | 6 ± 0.4 | 6 ± 0.4 | 6 ± 0.4 | 6 ± 0.4 | 6 ± 0.4 | 6 ± 0.4 |
| | T | 7 ± 0.2 | 7 ± 0.2 | 8 ± 0.2 | 8 ± 0.2 | 8 ± 0.2 | 8 ± 0.2 |
| (−)-Phenylephrine | U | 6 ± 0.4 | 6 ± 0.4 | 6 ± 0.4 | 6 ± 0.4 | 6 ± 0.4 | 6 ± 0.4 |
| | T | 6 ± 0.4 | 6 ± 0.4 | 7 ± 0.4 | 9 ± 0.4 | 9 ± 0.4 | 9 ± 0.4 |
| (−)-Ephedrine | U | 6 ± 0.4 | 6 ± 0.4 | 6 ± 0.4 | 6 ± 0.4 | 6 ± 0.4 | 6 ± 0.4 |
| | T | 6 ± 0.4 | 6 ± 0.4 | 6 ± 0.4 | 6 ± 0.4 | 6 ± 0.4 | 6 ± 0.4 |
| DRUG (2%) | | | | | | | |
| (−)-Pseudoephedrine | U | 7 ± 0.4 | 7 ± 0.4 | 7 ± 0.4 | 7 ± 0.4 | 7 ± 0.4 | 7 ± 0.4 |
| | T | 7 ± 0.4 | 7 ± 0.4 | 8 ± 0.4 | 8 ± 0.4 | 8 ± 0.4 | 10 ± 0.4 |
| (+)-Pseudoephedrine | U | 6 ± 0.4 | 6 ± 0.4 | 6 ± 0.4 | 6 ± 0.4 | 6 ± 0.4 | 6 ± 0.4 |
| | T | 6 ± 0.4 | 6 ± 0.4 | 7 ± 0.4 | 7 ± 0.4 | 7 ± 0.4 | 7 ± 0.4 |
| (−)-Phenylephrine | U | 6 ± 0.2 | 6 ± 0.2 | 12 ± 0.2 | 12 ± 0.2 | 12 ± 0.2 | 12 ± 0.2 |
| | T | 6 ± 0.2 | 6 ± 0.2 | 12 ± 0.2 | 12 ± 0.2 | 12 ± 0.2 | 12 ± 0.2 |
| (−)-Ephedrine | U | 5 ± 0.2 | 5 ± 0.2 | 9 ± 0.2 | 9 ± 0.2 | 9 ± 0.2 | 9 ± 0.2 |
| | T | 5 ± 0.2 | 5 ± 0.2 | 9 ± 0.2 | 9 ± 0.2 | 9 ± 0.2 | 9 ± 0.2 |

Results are as mean ± S.E. of five-six rabbits per drug.
U = Untreated contralateral eye
T = Drug treated eye

TABLE 7

Mydriatic Responses

| DRUGS | TREATED EYE | UNTREATED EYE |
|---|---|---|
| SALINE | 0 | 0 |
| (−)-Pseudoephedrine | 1% + | 1% 0 |
| | 2% ++ | 2% 0 |
| (+)-Pseudoephedrine | 1% + | 1% 0 |
| | 2% + | 2% 0 |
| (−)-Phenylephrine | 1% ++ | 1% 0 |
| | 2% +++ | 2% +++ |
| (−)-Ephedrine | 1% 0 | 1% 0 |
| | 2% +++ | 2% +++ |

SCALE: 0 = No change; + = 0–2 mm change; ++ = 2–4 mm change; +++ >4 mm change

EXAMPLE 3

(−)-Pseudoephedrine Central Nervous System Effects

Many sympathomimetic compounds stimulate the central nervous system. This is one reason that decongestants have side effects like insomnia. These tests compare the degree of central nervous system stimulation for (−)-pseudoephedrine with (+)-pseudoephedrine, (−)-ephedrine and (−)-phenylephrine. (−)-Pseudoephedrine gives rise to weak or negligible stimulation of the central nervous system.

Decongestants are often sold in combination with other active ingredients (e.,g. CLARITIN-D® and SELDANE-D®). In products containing two or more active ingredients, interactions between the active ingredients are undesirable. In these tests, the extent of (−)-pseudoephedrine interaction with a known antihistamine, tripolidine, was observed and compared to any such interaction between tripolidine and (+)-pseduoephedrine, (−)-ephedrine and (−)-phenylephrine.

Methods

Animals

Male Swiss-Webster mice (HSD ND4, Harlan Sprague Dawley, Houston, Tex.) aged 2–3 months were used in these studies. Each dose group consisted of 8 mice. The mice were housed 2 to 4 per cage in 30.4×22.9×15.2 cm clear polycarbonate cages with food and water available ad libitum for at least one week prior to locomotor activity testing. The colony was maintained at 23±1° C., on a normal light-dark cycle beginning at 0700 hr. All testing took place during the light portion of the light-dark cycle.

Apparatus

Horizontal (forward movement) locomotor activity was measured using a standardized, optical activity monitoring system [Model KXYZCM (16), Omnitech Electronics, Columbus, Ohio]. Activity was monitored in forty 40.5×40.5×30.5 cm clear acrylic chambers that where housed in sets of two within larger sound-attenuating chambers. A panel of 16 infrared beams and corresponding photodetectors were spaced 2 cm apart along the sides and 2.4 cm above the floor of each activity chamber. A 7.5-W incandescent light above each chamber provided dim illumination via a rheostat set to 20% of full scale. Fans provided an 80-dB ambient noise level within the chamber.

Drugs (−)-Pseudoephedrine, (+)-pseudoephedrine, (−)-phenylephrine and (−)-ephedrine were obtained from Sigma Chemical Co. Triprolidine HCl was obtained from Research Biochemicals International, (Natick, Mass.). All compounds were dissolved in 0.9% saline and injected i.p. in a volume of 10 ml/kg body weight, except for (−)-pseudoephedrine, which was dissolved in 0.16% tartaric acid in deionized water.

Procedure

Locomotor Stimulant Effects

In these studies, mice were placed in the activity testing chambers immediately following injection of saline or a dose of one of the test compounds ranging from 0.1 mg/kg to 250 mg/kg. (+)-Amphetamine was used as a positive control. The total horizontal distance traversed (cm) was recorded at 10 minute intervals for a 2-hour session. Separate groups of 8 mice were assigned to each dose or saline group, and dose-effect testing continued for each compound until maximal stimulant or depressant effects could be estimated. A separate control group was tested along with each compound.

For compounds with significant stimulant effects, the potency and efficacy were estimated for the 30-minute time period in which maximal stimulant effects were observed at the lowest dose. Using TableCurve 2D v2.03 (Jandel Scientific), the mean average total distance traversed (cm/10 min) for that period was fit to a 3-parameter logistic peak function of $\log_{10}$ dose (with the constant set to the mean of the saline group), and the maximum effect estimated from the resulting curve. The $ED_{50}$ (dose producing ½ maximal stimulant activity) was estimated from a linear regression against $\log_{10}$ dose of the ascending portion of the dose-effect curve. The stimulant efficacy was the peak effect of the compound (cm/10 min) as estimated from the logistic peak function, minus the mean control distance traveled (cm/10 min), and was expressed for each stimulant compound as a ratio to the stimulant efficacy determined for (+)-amphetamine.

For compounds with significant depressant effects, the potency and efficacy were estimated for the 30-minute time period in which maximal depression occurred at the lowest dose. The mean average total distance traversed (cm/10 min) for that period were fit to a linear function of $\log_{10}$ dose of the descending portion of the dose-effect curve. The $ID_{50}$ was the dose producing ½ maximal depressant activity, where maximal depression=0 cm/30 min. Efficacy was the ratio of maximal depressant effect to maximum possible depression for each compound (mean average total distance of the control group minus the lowest mean total distance, expressed as a ratio to the control group total distance).

$H_1$ Receptor Antagonist Interaction Studies

The potential for each compound to interact with $H_1$ antihistamine was determined by testing whether a known antihistamine, triprolidine, produced a dosage shift in the observed stimulant or depressant effects of each sympathomimetic compound. Triprolidine was used as an example of the class of $H_1$ receptor antagonists that are typically used as antihistaminic drugs. Twenty minutes prior to administering each test sympathomimetic compound, either tripolidine (at 0.01, 0.1, 1.0, or 25 mg/kg) or saline was injected. The mice were immediately placed in the activity testing chamber for a 2-h session. Doses of the test compound were selected from the ascending or descending time of the dose-effect curve determined from the compound-alone studies. Eight mice were tested for each triprolidine/sympathomimetic combination.

Statistical Analysis

Time course data for each compound were considered in 2-way analyses of variance with dose as a between-group and time as a within-group factor. The dose-effect data were considered in 1-way analyses of variance, and planned individual comparisons were conduced between each dose and the saline control group. Interaction studies were considered in 2-way analyses of variance, with Pretreatment and Test dose as the factors.

Results

The effects of sympathomimetic enantiomers on locomotor activity are summarized in Table 8.

Locomotor Stimulant Effects

Time Course

Mice injected with (+)-amphetamine showed a dose- and time-dependent increase in the distance traversed within 10 minutes following injection. The peak stimulant effects occurred during the first 30 minutes following 2.5 mg/kg and continued for at least 60 minutes.

(−)-Ephedrine resulted in increased locomotion within 40 minutes following 50 to 100 mg/kg, with peak effects occurring 60 to 90 minutes following injection and diminishing thereafter.

Little or no stimulant effects were evident within two hours following treatment with (−)-phenylephrine. (+)-Pseudoephedrine and (−)-pseudoephedrine gave rise to negligible stimulation compared to (−)-ephedrine, but weak stimulation when comared to (+)-amphetamine. (Table 8).

Locomotor Depressant Effects
Time Course (+)-Amphetamine and (−)-ephedrine treatment did not cause locomotor depression. However, treatment with (+)-pseudoephedrine, (−)-pseudoephedrine, and (−)-phenylephrine did result in some locomotor depression within 10 to 20 minutes following injection. These effects lasted from 20 minutes to ≧2 hours, depending upon dose and compound.

Depressant Efficacy/potency

Dose-response relationships for locomotor depressant effects of the sympathomimetics are provided in Table 8, for the time period in which the maximal depressant effects were first observed as a function of dose. The maximal depressant effect was the difference between the control group mean and the mean of the dose group with lowest locomotor activity. The maximum possible effect was assumed to be equivalent to the mean of the control group. Depressant efficacy was the ratio of maximal depressant effect to the maximum possible effect. Depressant efficacy did not substantially differentiate most of the compounds. The $ID_{50}$ for depressant effects was estimated from a linear regression through the descending portion of the dose-effect curve, assuming zero locomotor activity (horizontal distance) as the maximal effect. The order of potency for the depression was:

(−)-phenylephrine>>(−)-pseudoephedrine>(+)-pseudoephedrine.

When tested for dose-response in mice pretreated with 0.01, 0.1, or 1.0 mg/kg triprolidine, (−)-pseudoephedrine, (−)-phenylephrine, and (−)-ephedrine did not show significant modification of stimulant or depressant effects.

Significant effects for pretreatment with triprolidine were only observed for (+)-pseudoephedrine and (−)-ephedrine. Locomotor depression produced by 25, 50 or 100 mg/kg (+)-pseudoephedrine was reversed following 0.01 mg/kg triprolidine, but no significant reversal was apparent following 1.0 mg/kg triprolidine. These results indicate that while (+)-pseudoephedrine may interact with $H_1$ antihistamine receptors, (−)-pseudoephedrine does not.

EXAMPLE 4

(−)-Pseudoephedrine Has Few Negative Cardiovascular Effects

Sympathomimetic drugs are structurally related to amphetamine and frequently increase systolic and diastolic blood pressure due to increased cardiac contractility, cardiac output and vasoconstrictor. In this study, higher doses of (−)-pseudoephedrine than (+)-pseudoephedrine were required to give rise to an equivalent increase blood pressure, indicating that when similar doses are given, (−)-pseudoephedrine has fewer cardiovascular effects than (+)-pseudoephedrine.

Methods

Experiments were performed on twelve(12) healthy, mongrel dogs of either sex (weight range 25–35 kg). All dogs were anesthetized with sodium pentobarbital (30 mg/kg/i.v.) and the trachea intubated. The dogs were mechanically

TABLE 8

| | | Stimulation | | | Depression | | |
|---|---|---|---|---|---|---|---|
| Compound | Range[1] | Efficacy[2] | Potency[3] | Time[4] | Efficacy[5] | Potency[6] | Time[7] |
| (−)-Pseudoephedrine | 5–100 | 0.21 | 14.6 | 80–110 | 0.84 | 38.5 | 10–40 |
| (+)-Pseudoephedrine | 1–100 | 0.21 | 12.6 | 40–70 | 0.58 | 72.4 | 10–40 |
| (−)-phenylephrine | 0.1–10 | 0 | — | 60–90 | 0.77 | 2.3 | 0–30 |
| (+)-ephedrine | 0.5–250 | 0.80 | 38.2 | 50–80 | 0.45 | 7.4 | 10–40 |

[1]Dose range tested.
[2]The ratio of the maximal stimulant effect of the test compound to the maximal effect of (+)-amphetamine.
[3]The dose resulting in ½ the maximal stimulant effect ($ED_{50}$) in mg/kg i.p.
[4]The 30-min period following injection in which the maximal stimulant effect occurred.
[5]The ratio of the maximal depressant effect to the maximum possible effect (zero locomotor activity)
[6]The dose resulting in ½ the maximal depressant effect ($ID_{50}$) in mg/kg i.p.
[7]The 30-min minute period following injection in which the maximal depression occurred.
[8]"—" denotes value not calculated Trdprolidine Interactions
Triprolidine Alone When injected immediately prior to testing, doses of triprolidine from 0.25 to 25 mg/kg failed to affect horizontal distance during the 2-hour test period. Dose-dependent depression of locomotion was observed following 50 and 100 mg/kg, beginning within 10-minutes following injection and lasting for 30 to 40 minutes. A separate one-way analysis of variance on average distance/10 min for the period 0–30 minutes following injection suggested a significant dose main effect where $F(8,102)=7.7$ and $p<0.00 1$, although individual comparisons of dose groups with control in that analysis verified that significant effects of triprolidine were restricted to the 50 and 100 mg/kg doses (ps<0.01).

ventilated using a Harvard respirator (15 ml/kg) to avoid hypoxia during the experiment. A fluid-filled catheter was implanted in a femoral vein to administer additional anesthesia as needed during the experiment and to administer a sympathomimetic drug intravenously (i.v.). A fluid-filled femoral artery catheter was implanted to monitor aortic pressure (AP). For the measurement of left ventricular pressure (LVP), a fluid-filled catheter was advanced into the left ventricle from the carotid artery. A gastric tube was advanced orally through the esophagus into the stomach to administer drugs. At the beginning of each experiment the catheters were connected to ISOTEC® pressure transducers (Cardiovascular Concepts, Arlington, Tex.) and calibrated using a mercury manometer.

Experimentation began after a steady state was assured after instrumentation. Resting values for LVP, dP/dt, mean aortic pressure (MAP), and heart rate (HR) were recorded. After resting control data were obtained, a sympathomimetic drug was administered i.v. in log doses (μg/kg) until a 10% or greater increase in mean arterial pressure was observed. There was a 2 min interval between bolus doses. After the i.v. dose response was completed, an average 4 hour period elapsed to permit arterial pressure to return to baseline prior to giving a drug intragastric administration. The dose for the intragastric administration was calculated as 5 times the i.v. dose required to increase mean arterial pressure 10%. Each dog received one drug (one experiment per drug). The drugs were: (−)-pseudoephedrine, (+)-pseudoephedrine, (−)-ephedrine and (−)-phenylephrine.

Data Collection and Analysis

On-line variables were recorded on a Coulbourn 8-channel chart recorder (Allentown, Pa.) and on an 8-channel Hewlett-Packard model 3968A tape recorder (San Diego, Calif.) for subsequent computer analysis. Computer analysis was done by using a custom software package (Dataflow, Crystal Biotech, Hopkinton Mass.). The program samples recorded data at 2 msec intervals over 10 consecutive beats. The following data were analyzed from the recorded variables: left ventricular systolic pressure (LVSP) and end-diastolic pressure (LVEDP), +dP/dt$_{max}$, heart rate (HR), and systolic (SBP), diastolic (DBP) and mean (MAP) arterial blood pressures. Dose response curves were drawn using GRAPHPAD PRISM® program (San Diego, Calif.).

Results

In general, lower doses of (+)-pseudoephedrine caused adverse changes in blood pressure than was required to achieve similar effects for (−)-pseudoephedrine. For example, Table 9 provides the intravenous doses required to increase mean arterial pressure (MAP) in an anethetized dog.

TABLE 9

| Drug | Intravenous Dose Needed to Increase MAP 10% Intravenously |
|---|---|
| (−)-pseudoephedrine | 1400 μg/kg |
| (+)-pseudoephedrine | 200 μg/kg |
| (−)-phenylephrine | 10 μg/kg |
| (−)-ephedrine | 100 μg/kg |

Hence, seven times as much (−)-pseudoephedrine as (+)-pseudoephedrine is needed to cause a 10% increase in MAP upon intravenous administration. Similarly, lower dosages of two other commonly used decongestants were required to cause a 10% increase in MAP than was required for (−)-pseudoephedrine. These data indicate that (−)pseudoephedrine may have fewer negative cardiovascular side effects than several commercially available decongestants, when similar dosages of these drugs are administered.

EXAMPLE 5

Decongestant Activity of (+)-Pseudoephedrine

The decongestant activity of (−)-pseudoephedrine, (+)-pseudoephedrine, (−)-ephedrine and (−)-phenylephrine were compared in normal and histamine-challenged rats.

Experimental Protocol

The method is based on one reported by Lung for the measurement of nasal airway resistance. Eighty Sprague Dawley rats (weight range 247–365 gram) anesthetized with sodium pentobarbital intraperitoneally (50 mg/kg). Rats were placed on a heating pad, in a V trough, dorsal side down. A tracheotomy was performed and the tracheal cannula was left open to room air. A cannula was placed into the superior part of the trachea and was advanced till ledged in the posterior nasal opening. Normal saline (0.5 ml) was injected into the nasal cavity to confirm position of the cannula as well as to moisten the nasal mucosa. After nasal cannulation was confirmed the cannula was tied in place with a suture placed around the trachea. Excess fluid was expelled from the nasal airway with a short (2–3 second) air flow via the nasal cannula. Additionally, in studies correlating blood pressure changes to those in the nasal airway pressure, a cannula was positioned in the internal carotid artery (PE.50) and connected to a multipen (Grass) recorder using pressure transducer (Isotec).

Nasal airway pressure was measured using a Validyne pressure transducer (with a 2.25 cm $H_2O$ range membrane) connected to a multipen recorder (Grass). Air was passed through an in-line direct measure flow meter (Gilmont instruments) connected to the nasal opening cannula. Pressure was measured in this line with a constant flow rate (150 ml/min) of air. Enantiomeric drugs were directly injected into the jugular vein using a 30 gauge needle. All injections were of a constant 0.1 ml volume. In the congestion challegened groups congestion was achieved by an intranasal administration of histamine (50 mM, 0.02 ml/nostril). The histamine was expelled after 2 min with a short nasal cannula airflow and subsequent enantiomeric drug doses were directly injected into the jugular vein. The doses of injection for each of the enantiomers tested were determined from a previous study in which each of the dose of drug we chose resulted in an increase in mean arterial pressure (MAP) of 10% (Table 10). The dose causing a 10% increase in MAP served as our "100%" dose for the initial nasal airway studies.

TABLE 10

Dosage of Enantiomer that Raised Mean Arterial Pressure 10%

| Drug Name | Dog (μg/kg) | Rat (μg) |
|---|---|---|
| (−)-pseudoephedrine | 1400 | 420 |
| (+)-pseudoephedrine | 200 | 60 |
| (−)-ephedrine | 100 | 30 |
| (−)-phenylephrine | 10 | 3–5 |

Two Investigations were Performed as Follows

Investigation 1

A comparison was made of the effect of the different enantiomers on nasal airway resistance prior to and following histamine-induced congestion. The amount of drug required to raise the mean arterial pressure by 10% was chosen as the "100% dose" for these decongestant studies. See Table 10. Control changes in nasal airway resistance were obtained by recording nasal airway resistance prior to and following this 100% dose. In a test group of rats the 100% dose was injected into the jugular vein two minutes after nasal airway congestion was produced by introduction of 0.02 ml/nostril of 50 mM histamine into the nasal airway. Nasal airway resistance was thus increased after the histamine challenge, and the effect of administering an enantiomer on this histamine-induced airway resistance was observed.

Investigation 2

A comparison of the effect of enantiomer dosage on nasal airway resistance was made to determine an effective dosage range of each enantiomer. Dosages tested were 50%, 25%, 10% and 5% of the "100%" enantiomer dosage required to increase the mean arterial pressure 10%. Changes in nasal airway resistance were obtained by comparing pre-enantiomer injection nasal airway resistance with decreases in nasal airway resistance following jugular vein injection of the enantiomer dosage. Five rats were tested at each dose for each of the enentiomers.

Results

Investigation 1

Each drug gave rise to a significant decrease in nasal airway pressure, relative to control, in non-histamine-challenged rats (Table 11). While the control for the (−)-phenylephrine was significantly different from the other controls, this difference in control level did not translate into a difference caused by administration of the drug.

TABLE 11

Mean Decrease in Nasal Airway Pressure

| Drug | Control (mm $H_2O$) | Post Drug (mm $H_2O$) | % Change | Paired t test p Value |
|---|---|---|---|---|
| (−)-pseudoephedrine | 9 ± 0.1 | 8 ± 0.2 | −12.0 ± 2.4 | 0.008 |
| (+)-pseudoephedrine | 9 ± 0.5 | 7 ± 0.9 | −21.3 ± 7.6 | 0.015 |
| (−)-ephedrine | 7 ± 0.8 | 6 ± 0.5 | −14 ± 3.4 | 0.034 |
| (−)-phenylephrine | 5 ± 0.2 | 4 ± 0.2 | −20.3 ± 4.3 | 0.010 |

*mm water.

In the histamine-challegened rats, administration of each drug again showed a significant decrease in nasal passage pressure (Table 12). It is unclear whether or not the drugs bind to histamine receptors.

TABLE 12

Mean Decrease in Nasal Airway Pressure

| Drug | Control* | t test p Value | Post* Histamine | T test p Value | Post* Drug | % Change |
|---|---|---|---|---|---|---|
| (−)-pseudoephedrine | 9.5 ± 1.9 | 0.4 | 10.5 ± 1.27 | 0.003 | 7.9 ± 1.1 | −24.7 ± 3.4 |
| (+)-pseudoephedrine | 6.6 ± 0.6 | 0.1 | 9.3 ± 1.8 | 0.001 | 6.1 ± 1.5 | −36.7 ± 2.7 |
| (−)-ephedrine | 6.7 ± 0.4 | 0.06 | 8.2 ± 0.7 | 0.007 | 6.4 ± 0.6 | −21.8 ± 3.5 |
| (−)-phenylephrine | 7.5 ± 0.5 | 0.04 | 13.2 ± 2.1 | 0.05 | 10.5 ± 2.1 | −22.3 ± 8.5 |

*mm water.

The results indicated that the decongestant activity of (−)-pseudoephedrine was as good as, or superior to, several commercially available decongestants.

Investigation 2

Table 13 summarizes the mean nasal airway pressure of different enantiomer dosages ranging from 5%, 10%, 25% and 50% of the dose that produces a 10% change in resting mean arterial pressure (the "100%" dose). The standard error of the mean is also provided.

TABLE 13

Mean Decrease in Nasal Airway Pressure With Variable Enantiomer Dosages*

| Drug# | 5% | 10% | 25% | 50% |
|---|---|---|---|---|
| (−)-pseudoephedrine | | −0.03 ± 0.8 | −0.5 ± 0.6 | −1.9 ± 4.4 |
| (+)-pseudoephedrine | −3.8 ± 2.8 | −6.8 ± 3.6 | −13.5 ± 4.3 | −16.1 ± 2.4 |
| (−)-ephedrine | −1.0 ± 0.8 | −2.5 ± 1.5 | − 3.6 ± 1.9 | −1.9 ± 2.0 |
| (−)-phenylephrine | −1.6 ± 0.9 | −4.8 ± 0.8 | −12.1 ± 2.4 | −5.2 ± 1.6 |

*Decreases in nasal airway pressure are provided in mm water with the indicated percent of the enantiomer dose that increased the dog resting mean arterial pressure 10%.

What is claimed:

1. A method of relieving nasal and bronchial congestion which comprises administering a pharmaceutically effective amount of (−)-pseudoephedrine to a mammal, wherein said (−)-pseudoephedrine is substantially free of (+)-pseudoephedrine.

2. The method of claim 1 wherein said method avoids a side effect related to administration of (+)-pseudoephedrine.

3. The method of claim 1 wherein said side effect is a drug interaction.

4. The method of claim 1 wherein said side effect is an interaction with an antihistamine.

5. The method of claim 1 wherein said (−)-pseudoephedrine is not readily converted to (S)-methamphetamine.

6. The method of claim 1 wherein said pharmaceutically effective amount is an amount of (−)-pseudoephedrine sufficient to activate an α-adrenergic receptor.

7. A method of dialating the pupil which comprises administering a pharmaceutically effective amount of (−)-pseudoephedrine topically to a mammal, wherein said (−)-pseudoephedrine is substantially-free of (+)-pseudoephedrine.

8. The method of claim 7 wherein said pharmaceutically effective amount is an amount of (−)-pseudoephedrine sufficient to activate an α-adrenergic receptor.

9. The method of claim 7 wherein said method has less side effects than administration of (+)-pseudoephedrine.

10. The method of claim 9 wherein said side effect is an increase in intraocular pressure.

* * * * *

UNITED STATES PATENT AND TRADEMARK OFFICE
CERTIFICATE OF CORRECTION

PATENT NO.     : 6,495,529 B1                                          Page 1 of 1
DATED          : December 17, 2002
INVENTOR(S)    : Anthony Booth et al.

It is certified that error appears in the above-identified patent and that said Letters Patent is hereby corrected as shown below:

<u>Column 5,</u>
Lines 16-22, should read
-- According to the present invention, (-)-pseudoephedrine does not interact with other drugs, for example, with antihistamines. This is one advantage that the present compositions and methods of using (-)-pseudoephedrine have over compositions and methods of using (+)-pseudephedrine: (-)-pseudoephedrine does not interact with $H_1$ antihistamines such as..... --

Signed and Sealed this

Eleventh Day of November, 2003

JAMES E. ROGAN
*Director of the United States Patent and Trademark Office*